United States Patent [19]

Gaisford

[11] Patent Number: 5,259,239
[45] Date of Patent: Nov. 9, 1993

[54] HYDROCARBON MASS FLOW METER

[76] Inventor: Scott Gaisford, Eikeveien 22, 4300 Sandnes, Norway

[21] Appl. No.: 866,387

[22] Filed: Apr. 10, 1992

[51] Int. Cl.$^5$ .......................... G01F 1/74; G01F 33/22
[52] U.S. Cl. .................... 73/61.44; 73/861.04
[58] Field of Search ................ 73/61.43, 61.44, 861.04

[56] References Cited

U.S. PATENT DOCUMENTS 4,802,361 2/1989 Bussian et al. ...................... 73/61.43

Primary Examiner—Herbert Goldstein
Attorney, Agent, or Firm—Flehr, Hohbach, Test, Albritton & Herbert

[57] ABSTRACT

A measurement apparatus which utilizes the direct relationship between the density and dielectric constant of hydrocarbon mixtures to significantly improve upon the measurement capabilities of some existing devices used in the petroleum industry. Included among the applications of the apparatus are 1) a multiphase hydrocarbon mass flow meter for usage with multiphase mixtures of oil, water, and gas and 2) a continuously self-calibrating water cut meter for determining the water content of liquid crude oil streams.

4 Claims, 3 Drawing Sheets

HYDROCARBON MASS FLOW METER

BACKGROUND OF THE INVENTION

This invention relates to the field of meters and particularly to meters for continuously measuring the composition and mass flow rate of mixtures containing hydrocarbons. Many types of measurement apparatus have been proposed and are being used for continuously measuring water content, density, or composition of hydrocarbon or hydrocarbon and water mixtures. But most suffer from a number of limitations caused by difficulties with measuring mixtures containing liquid and gas or difficulties associated with variations in the specific gravity of the hydrocarbon being measured. Measuring the composition of oil, water, and gas mixtures is one example. Meters for this purpose are typically referred to as multiphase composition meters. See U.S. Pat. Nos. 4,458,524 and 4,760,742 and U.K. Patent 2,210,461.

The current practice in the oil industry for measuring the quantities of oil, water, and gas being produced by a given well or group of wells is to separate the components in a separator and measure the components individually. The separators are large, expensive, maintenance intensive, and typically provide production information only at long intervals. With continuous multiphase meters to replace the separators, oil producers can dramatically improve the crude oil and natural gas production process, particularly offshore production.

Most proposed multiphase composition meters are designed to continuously measure the volume fractions of oil, water, and gas being produced. The composition meter can be combined with a flowmeter such that production rates for the three components can be calculated. One variety of proposed multiphase composition meter combines a dielectric constant measurement means with a density measurement means. See, for example, U.S. Pat. No. 4,458,524. These devices take advantage of the different dielectric constant and densities of oil, water, and gas respectively to determine their volume fractions. Temperature and pressure sensors are included in the metering package to facilitate these calculations.

In order for them to function properly, they must be able to calculate the dielectric constants and/or densities of the three individual components at the measurement conditions. This is impossible. Several of the lower-density hydrocarbon components (ethane, propane, butane, and pentane among them) can exist in either a liquid or a gaseous state at pressures between 20 and 250 atm. Therefore, the fundamental methods and equations used by these meters to determine the composition of the multiphase production streams are flawed. In fact, it is not possible to accurately determine the volume fractions of oil, water, and gas without knowing how much of each hydrocarbon constituent is in the liquid or gaseous phase at any given time. Such information is not available on a continuous basis.

Another important measurement problem in the oil industry is the accurate measurement of the water content of liquid crude oil streams. The water content directly affects the price paid for crude oil. Many devices have been developed to continuously measure the water content. See U.S. Pat. Nos. 3,498,112 and 4,862,060 for examples. The most commonly used measurement device for this application is a capacitance meter which measures the dielectric constant of the mixture to determine its water content. Many meters besides capacitance meters utilize dielectric measurements for measuring the water content of crude oils, including various microwave meters. A common problem for all of these devices is that the density and dielectric constant of the crude oil vary over time. These variations result directly in significant measurement error.

SUMMARY OF INVENTION

To avoid the problems associated with measuring multiphase flow where the physical properties of the liquid and gaseous hydrocarbon cannot be determined, it is appropriate to consider the hydrocarbon liquids and gases as a single component with an unknown density. A suitable multiphase composition meter would then determine the volumetric fraction and the density of the hydrocarbon, i.e. the mass, of the hydrocarbon material in a multiphase mixture and the water content of the mixture. Armed with this information plus flow rate information, the user can more correctly determine how much oil and gas are being produced at standard conditions.

Therefore, a multiphase hydrocarbon mass meter to be used in crude oil or natural gas multiphase production lines is considered desirable. One embodiment of this invention combines a dielectric measurement means, a density measurement means, and a temperature measurement means to determine the instantaneous hydrocarbon mass flowing through the meter. The present invention utilizes a heretofore unknown relationship between the density of a hydrocarbon, whether liquid, gas or a combination thereof, and its dielectric constant.

As with the multiphase hydrocarbon mass meter, an improved meter to measure water content (i.e. a water cut meter) which consists of a combination of a dielectric measurement means, a density measurement means, and a temperature measurement means makes it possible to continuously correct the water cut meter for variations in the oil's dielectric properties. Combining this improved water cut meter with a flow meter give the additional possibility of continuously totalizing the production rates of the oil and water in terms of volume or mass per unit of time and continuously measuring the crude oil quality which is directly related to its density. This improved water cut meter is useful with crude oils, gas condensates, and liquid natural gases.

It is an object of the invention to provide an improved multiphase measuring apparatus for measuring the instantaneous hydrocarbon mass and mass flow rate in a crude oil or natural gas production line containing primarily oil, water, and gas.

It is an object of the invention to provide an apparatus which includes measurement means for measuring mixture dielectric constant, density, and temperature.

It is an object of the invention to provide an apparatus for determining the instantaneous hydrocarbon mass contained in the apparatus in accordance with the measured dielectric constant, density, and temperature.

It is an object of the invention to provide an apparatus which includes an instantaneous hydrocarbon mass meter and a flow rate meter.

It is an object of the invention to provide an apparatus for determining the hydrocarbon mass flow rate in accordance with the measured instantaneous hydrocarbon mass and its flow rate.

It is the object of the invention to provide an improved water cut meter for continuously measuring the water content and liquid hydrocarbon density in a crude oil or liquid natural gas production line containing primarily liquid hydrocarbon and water.

It is an object of the invention to provide an apparatus which includes measurement means for measuring mixture dielectric constant, density, and temperature.

It is an object of the invention to provide an apparatus for determining the instantaneous hydrocarbon density and water content contained in the apparatus in accordance with the measured dielectric constant, density, and temperature.

It is an object of the invention to provide an apparatus which continuously calibrates itself for changes in the dielectric constant of the liquid hydrocarbon so as to more accurately measure the water content of the liquid hydrocarbon.

It is an object of the invention to provide an apparatus which combines the self-calibrating water cut meter with a flow meter.

It is an object of the invention to provide an apparatus for determining the liquid hydrocarbon and water volumetric production rates or mass flow rates in accordance with the measured water content, liquid hydrocarbon density, and flow rate.

DESCRIPTION OF THE INVENTION

Theory

Prior Art multiphase fraction meters which comprise a device for measuring the dielectric constant and the density of the mixture implement the following relations to determine the volume fractions of oil, water, and gas:

$$1 = V_w + V_o + V_g \qquad \text{Eq. 1}$$

$$\rho_{mix} = \rho_w V_w + \rho_o V_o + \rho_g V_g \qquad \text{Eq. 2}$$

$$e_{mix} = f(e_w, e_o, e_g, V_w, V_o) \qquad \text{Eq. 3}$$

where
 'w' is the subscript for water,
 'o' is the subscript for oil,
 'g' is the subscript for gas,
 'mix' is the subscript for the multiphase mixture,
 V = Volume fraction,
 $\rho$ = Density,
 e = dielectric constant.

Equation 3 is any of a number of equations which describe the relationship between the dielectric constant of the mixture and the dielectric constants and volume fractions of the components. For example, one might use the Looyenga mixing relation:

$$e_{mix} = [V_w e_w^{\frac{1}{3}} + V_o e_o^{\frac{1}{3}} + V_g e_g^{\frac{1}{3}}]^3.$$

In these equations, the volume fraction $V_w$, $V_o$, and $V_g$ are to be calculated from the measured mixture density $\rho_{mix}$ and dielectric constant $e_{mix}$. The dielectric constant and densities of the three components vary with temperature and pressure. Therefore, the appropriate values must be calculated at the measurement temperature and pressure if the procedure is to work. This can be done if the physical properties of the oil, water, or gas taken separately do not change with temperature and pressure in an unpredictable fashion. But, such is not the case. Several of the hydrocarbon components can be in either the liquid or gaseous state at higher pressures; therefore, the oil and gas densities and dielectric constants are unknown at high pressure.

The method and apparatus of this invention differ from this standard approach by considering the oil and gas components as a single hydrocarbon material with an unknown density and dielectric constant. The invention utilizes the principal that the dielectric constant and density of hydrocarbons produced by oil wells can be directly related to one another. This is true if the hydrocarbon is liquid, gas, or a combination thereof.

Figure 1:
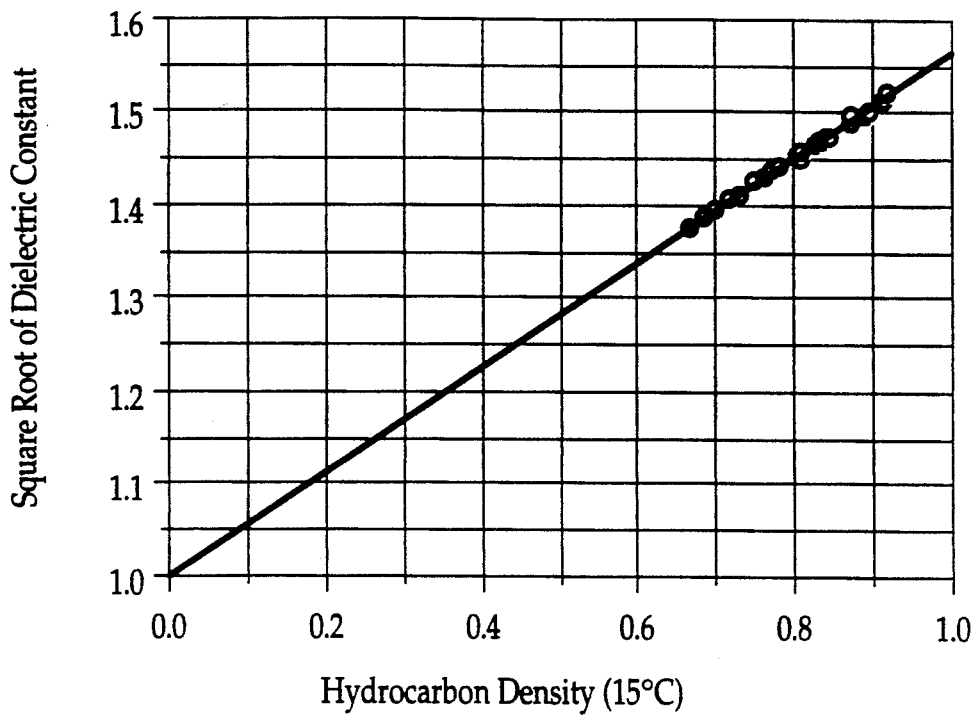
FIGS. 1 and 2 are plots of the square root of the dielectric constant versus hydrocarbon density for liquid hydrocarbons and hydrocarbon/gas mixtures respectively.
Figure 2:
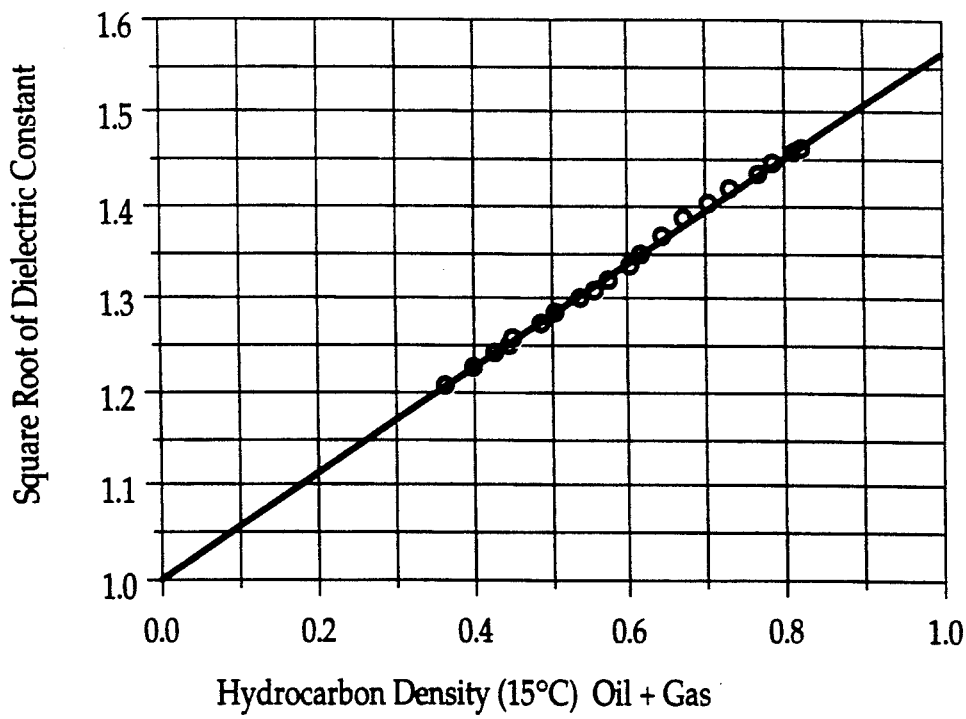

This principle is illustrated in FIGS. 1 and 2. FIG. 1 shows the square root of the measured dielectric constant versus density for a variety of hydrocarbon liquids at 15° C. A linear curve fit is also shown in the figure. The lowest density hydrocarbon is pentane with a density of approximately 0.67 g/ml. The highest density hydrocarbon is a heavy crude oil having a density of approximately 0.92 g/ml. Included among the hydrocarbons shown in FIG. 1 are crude oils, gas condensates, and individual hydrocarbon fractions. As FIG. 1 shows, the square root of the dielectric constant and the density of hydrocarbon liquids are linearly related with the zero density intercept being 1. In other words, as the density approaches zero, the dielectric constant approaches 1 which is the dielectric constant of vacuum which has a density of zero.

FIG. 2 shows the square root of the dielectric constant as a function of density for a crude oil mixed with varying amounts of gas. The volummetric fraction of gas extends from 0 to 55%. Here too, the relationship between the square root of the dielectric constant and the density is linear and the zero density intercept is 1. In this case the dielectric constant of the gas is approximately equal to 1.0005.

The linear curve fits in FIGS. 1 and 2 are virtually identical. In practice, the slope of these curves varies slightly with temperature. This demonstrates the important principal that the density of a hydrocarbon, whether liquid, gas or a combination thereof, can be related accurately to its dielectric constant. This principal is the foundation of this invention. The principal has heretofore not been recognized in the scientific literature (to our knowledge) nor has it been utilized in the design of multiphase meters or water cut meters.

The relationship between hydrocarbon dielectric constant and density can be used to avoid the problems associated with measuring liquid and gas hydrocarbon fractions at high pressure. Instead of measuring oil, water, and gas fractions, the multiphase meter can instead measure hydrocarbon and water fractions and the density of the hydrocarbon; i.e. the multiphase hydrocarbon mass meter continuously measures the mass of the hydrocarbon being produced. Instead of using Equations 1 to 3, the multiphase hydrocarbon mass meter would use a measurement procedure illustrated by the following relations:

$$1 = V_w + V_{hyd} \qquad \text{Eq. 4}$$

$$\rho_{mix} = \rho_w V_w + \rho_{hyd} V_{hyd} \qquad \text{Eq. 5}$$

$$e_{mix} = f(e_w, e_{hyd}, V_w, V_{hyd}) \qquad \text{Eq. 6}$$

where

'hyd' is the subscript for hydrocarbon.

Equation 4 could be any of a number of equations which describe the relationship between the dielectric constant of a mixture and the dielectric constant and volume fractions of its components. The following relation could be used for example:

$$e_{mix} = [V_w e_w^{\frac{1}{3}} + V_{hyd} e_{hyd}^{\frac{1}{3}}]^3.$$

In Equations 4–6, there are three unknowns: $V_{hyd}$, $\rho_{hyd}$, and $e_{hyd}$. But the dielectric constant and the density of the hydrocarbon can be related using the principal illustrated in FIGS. 1 and 2, namely:

$$\sqrt{e_{hyd}} = (A * \rho_{hyd}) + 1 \qquad \text{Eq. 7}$$

where

'A' is a constant which is a function of temperature. For one specific temperature, 'A' is the slope of the curves shown in FIGS. 1 and 2.

Using this relation, the component relations reduce to the following three equations;

$$1 = V_w + V_{hyd} \qquad \text{Eq. 8}$$

$$\rho_{mix} = \rho_w V_w + \rho_{hyd} V_{hyd} \qquad \text{Eq. 9}$$

$$e_{mix} = f(e_w, \rho_{hyd}, V_w, V_{hyd}) \qquad \text{Eq. 10}$$

Thus, by measuring the mixture dielectric constant ($e_{mix}$) and mixture density ($\rho_{mix}$) and calculating the dielectric constant ($e_w$) and density ($\rho_w$) of the water at the measurement temperature, it is possible to determine the hydrocarbon fraction ($V_{hyd}$) and the hydrocarbon density ($\rho_{hyd}$) in the mixture. Such is the basis for the multiphase hydrocarbon mass meter which measures both the instantaneous mass of hydrocarbon contained in a multiphase mixture and the water content of the mixture. The instantaneous mass is equal to $V_{hyd} \times \rho_{hyd}$. This meter when combined with a flow meter makes it possible to measure the mass flow rate of the hydrocarbon and water respectively.

The principle of the self-calibrating water cut meter is much the same. Water cut meters which are based on a measurement of the dielectric properties of liquid hydrocarbon and water mixtures to determine the water content are based a dielectric mixing law such as Equation 3, but simplified for two components. We have:

$$e_{mix} = f(e_w, e_o, V_w, V_o) \qquad \text{Eq. 11}$$

where

'w' is the subscript for water,
'o' is the subscript for oil,
'mix' is the subscript for the multiphase mixture,
V = Volume fraction,
e = dielectric constant.

Equation 11 could be any of a number of dielectric mixing laws such as:

$$e_{mix} = [V_w e_w^{\frac{1}{3}} + V_o e_o^{\frac{1}{3}}]^3.$$

In order for the principle to be applied accurately, the dielectric constant of the liquid hydrocarbon must remain constant over time. Unfortunately, this is not usually the case. The dielectric constant of the liquid hydrocarbon produced by individual wells varies. The situation is even more complex when the liquid being measured is the commingled flow of many different wells. For commingled flow the dielectric constant of the hydrocarbon can change significantly as the production rates of the different feeder lines vary. This problem (among others) means that existing water cut meters do not deliver sufficient accuracy for many of the more crucial applications in the oil industry.

One can take advantage of the close relationship between hydrocarbon density and dielectric constant as illustrated in FIG. 2 to alleviate this problem. Combining a density measurement means with the dielectric constant measurement means and temperature measurement means, one can correct for variations in the hydrocarbon dielectric constant by determining it density continuously. One has the following relations:

$$1 = V_w + V_o \qquad \text{Eq. 12}$$

$$\rho_{mix} = \rho_w V_w + \rho_o V_o \qquad \text{Eq. 13}$$

$$e_{mix} = f(e_w, e_o, V_w, V_o) \qquad \text{Eq. 14}$$

$$\sqrt{e_o} = (A * \rho_o) + 1 \qquad \text{Eq. 15}$$

where

A is a constant which is a function of temperature.

By combining the density measurement means, the dielectric measurement means and by using these relations, the improved water cut is able to use the density information to adjust the dielectric constant of the crude oil as it changes over time. In other words, by simultaneously solving the relations for water cut and mixture density as expressed in Equations 13 and 14, the improved water cut meter calibrates itself for changes in the oil's dielectric properties over time. This is what is meant by self-calibrating water cut meter.

Multiphase Hydrocarbon Mass and Mass Flow Meter

Figure 3:
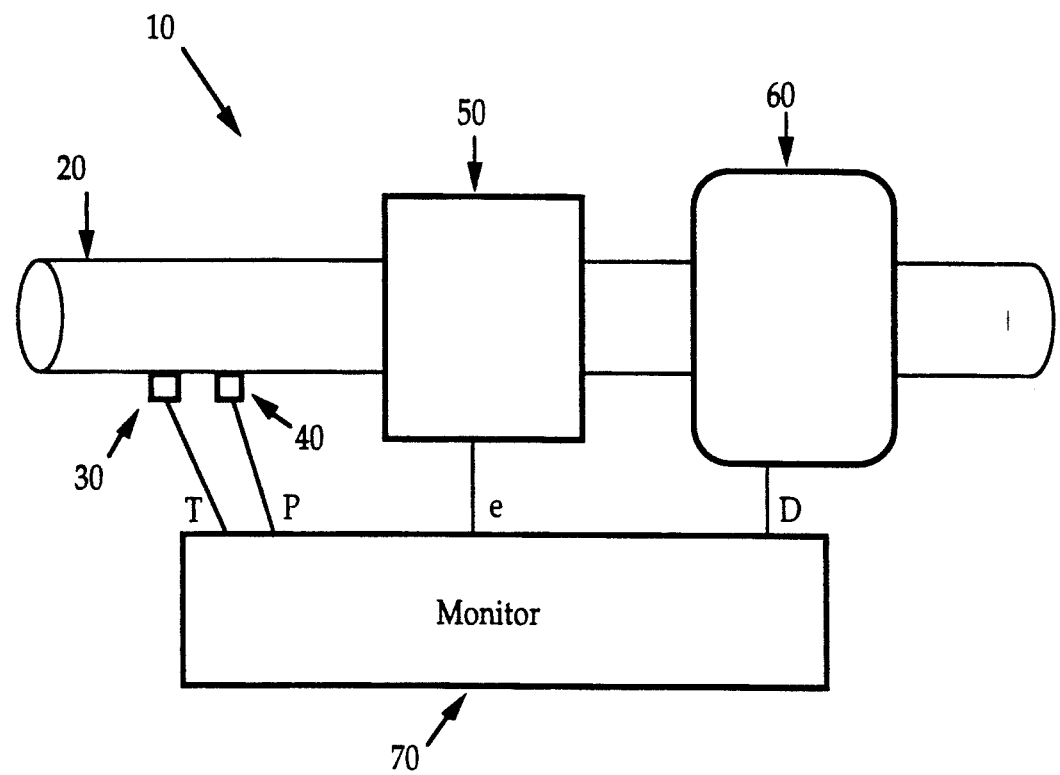
FIG. 3 is a block diagram of a multiphase hydrocarbon mass meter constructed in accordance with the present invention.

The novel relation between a hydrocarbons density and its dielectric constant as shown in the foregoing theoretical section is used in this embodiment of the present invention as a means of determining hydrocarbon mass and mass flow rate. With reference to FIG. 3, the production stream, consisting of water, crude oil, and gas, flows through a multiphase hydrocarbon mass meter generally designated by the numeral 10. Apparatus 10 includes a fluid flowing conduit 20 through which the mixture passes. The mixture to be measured may be conducted through conduit 20 on a continuous basis and conduit 20 may comprise part of a mixture transmission pipeline. Temperature measurement means 30 measures the temperature 'T' of the mixture. An optional pressure measurement means 40 measures the pressure 'P' of the mixture. Apparatus 10 includes a dielectric measurement means 50 for measuring the dielectric properties 'e' of the mixture. Dielectric measurement means 50 may be any of a variety of devices for measuring the dielectric properties of flowing material such as a capacitance meter or a microwave meter. Apparatus 10 includes a density measurement means 60 which measures the density 'D' of the mixture. Density measurement means 60 may by any device capable of measuring the density of multiphase mixtures. One such device would be a gamma densitometer.

Temperature measurement means 30, pressure measurement means 40, dielectric measurement means 50, and density measurement means 60 are connected to multiphase hydrocarbon mass measurement means 70 and provide signals corresponding to the measured T, P, e, D values. Multiphase hydrocarbon mass measurement means 70 calculates the correct density and dielectric constant for the water from the measured temperature (and pressure). From these values and e and D, multiphase hydrocarbon mass measurement means 70 provides an indication of the volumetric water content, the volumetric hydrocarbon content, and the hydrocarbon density. The product of the hydrocarbon density and the hydrocarbon volumetric content is equal to the hydrocarbon mass 'M'.

Figure 4:
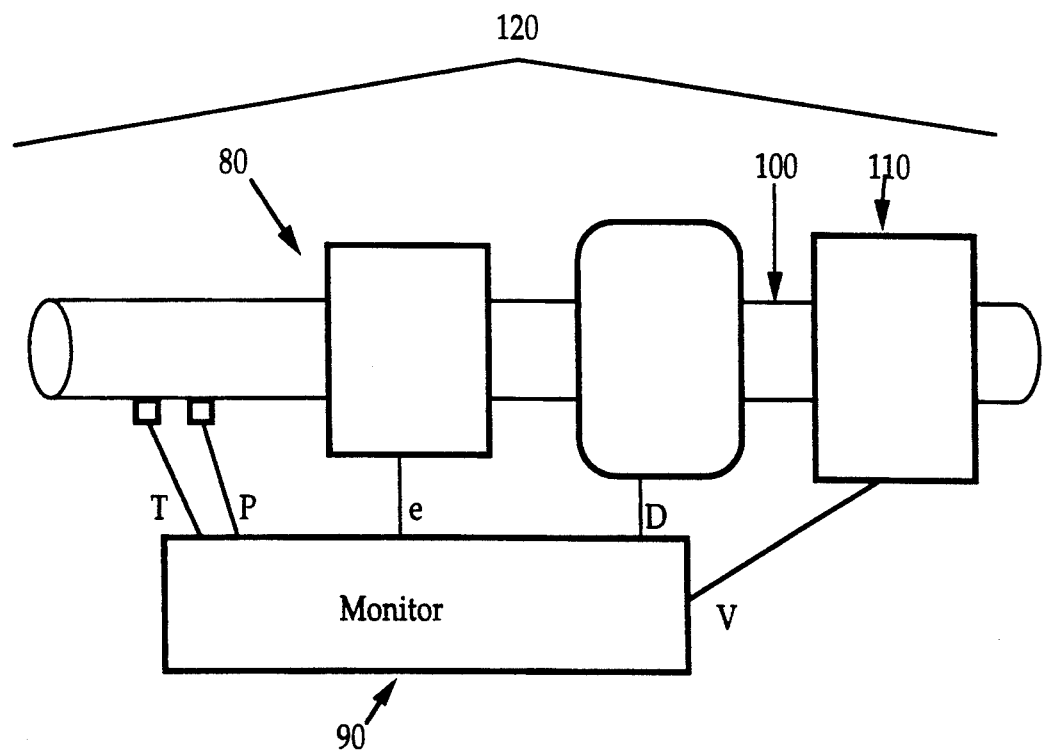
FIG. 4 is a block diagram of a hydrocarbon mass flow meter constructed in accordance with the present invention.

Referring now to FIG. 4, multiphase hydrocarbon mass meter 80 is connected to a flow rate measurement means 110 with a pipe section 100. The combined apparatus is a multiphase hydrocarbon mass flow meter and is designated as 120. The multiphase mixture can flow freely through the multiphase hydrocarbon mass flow meter 120. Flow rate measurement means 100 measures the flow rate V of the mixture as it passes and provides a corresponding flow rate signal to multiphase hydrocarbon mass measurement means 90. Multiphase hydrocarbon mass measurement means 90 provides an indication of the hydrocarbon mass flow rate in accordance with the received signal V and the measured value M.

Numerous variations and modifications can be made without departing from the invention. For example, many types of temperature measurement means, pressure measurement means, dielectric measurement means, density measurement means, or flow rate measurement means could be used as components of the multiphase hydrocarbon mass flow meter. Moreover, the design of measurement means 70 or 90 could take on many forms. Different combinations of analog to digital converters, digital to analog converters, comparators, look up tables, microprocessors, etc. could be used to determine the instantaneous hydrocarbon mass and mass flow rate from the input signals. Accordingly, it should be clearly understood to anyone skilled in the art that the form of the invention described above and shown in the figures is general in nature and not intended to limit the scope of the invention to any specific component measurement means within the scope and spirit of the appended claims.

Self-Calibrating Water Cut Meter

The novel relation between a hydrocarbons density and its dielectric constant at shown in the theoretical section is used in this embodiment of the present invention as a means of determining the water cut corrected for the changing dielectric constant of the liquid hydrocarbon. In addition the relation makes possible the continuous determination of the density of the hydrocarbon, corrected for the water content, and its mass flow rate. In illustrating this embodiment, reference will be made to FIGS. 5 and 6.

Figure 5:
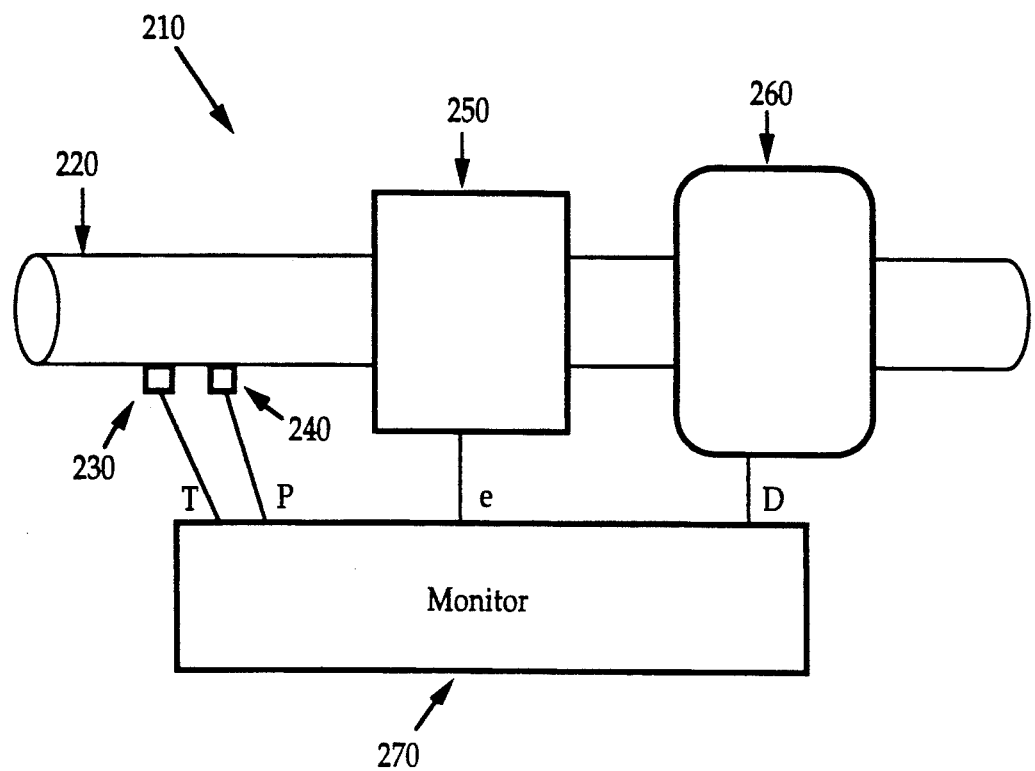
FIG. 5 is a block diagram of an improved water cut meter constructed in accordance with the present invention.

With reference to FIG. 5, the production stream, consisting of water and liquid hydrocarbon such as crude oil, LNG, or LPG, flows through a self-calibrating water cut meter generally designated by the numeral 210. Apparatus 210 includes a fluid flowing conduit 220 through which the mixture passes. The mixture to be measured may be conducted through conduit 220 on a continuous basis and conduit 220 may comprise part of a mixture transmission pipeline. Temperature measurement means 230 measures the temperature 'T' of the mixture. An optional pressure measurement means 240 measures the pressure 'P' of the mixture. Apparatus 210 includes a dielectric measurement means 250 for measuring the dielectric properties 'e' of the mixture. Dielectric measurement means 250 may be any of a variety of devices for measuring the dielectric properties of flowing materials such as a capacitance meter or a microwave meter. Apparatus 210 includes a density measurement means 260 which measures the density 'D' of the mixture. Density measurement means 260 may be any device capable of measuring the density of multiphase mixtures. The density measurement means could be a gamma densitometer, a Coriolis Meter, or a vibrating fork densitometer for example.

Temperature measurement means 230, pressure measurement means 240, dielectric measurement means 250, and density measurement means 260 are connected to water cut measurement means 270 and provide signals corresponding to the measured T, P, e, D values. Water cut measurement means 270 calculates the correct density and dielectric properties for the water from the measured temperature (and pressure). From these values and e and D, water cut measurement means 270 provides an indication of the instantaneous water cut 'W' and the hydrocarbon density 'B' in conduit 220.

Figure 6:
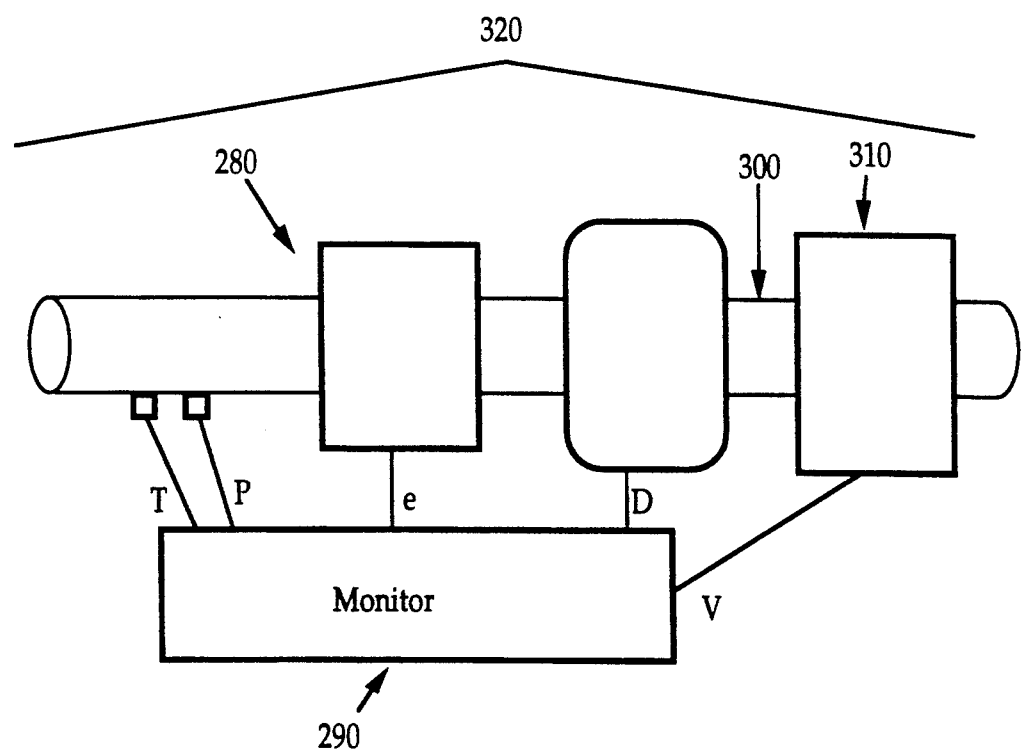
FIG. 6 is a block diagram of an oil and water mass flow meter constructed in accordance with the present invention.

Referring now to FIG. 6, water cut meter 280 is connected to a flow rate measurement means 310 with a pipe section 300. The combined apparatus is an oil and water mass flow meter and is designated as 320. The water and oil mixture can flow freely through the crude oil mass flow meter 300. Flow rate measurement means 310 measures the flow rate V of the mixture as it passes and provides a corresponding flow rate signal to water cut measurement means 290. Water cut measurement means 290 provides an indication of the hydrocarbon mass flow rate in accordance with the received signal V and the measured values W and B. In fact the hydrocarbon mass flow rate is the product of $V \times B \times (1-W)$.

Numerous variations and modifications can be made without departing from the invention. For example, many types of temperature measurement means, pressure measurement means, dielectric measurement means, density measurement means, or flow rate measurement means could be used as components of the hydrocarbon mass flow meter. Moreover, the design of measurement means 270 and 290 could take on many forms. Many different combinations of analog to digital converters, digital to analog converters, comparators, look up tables, microprocessors, etc. could be used to determine the instantaneous hydrocarbon mass and mass flow rate from the input signals. The basic concept of using the density signal to correct for the changing dielectric constant of one of the base components of a mixture could be used for more accurately determining the composition of any mixture containing a high dielectric constant material such as water in a low dielectric constant material such as oil. Accordingly, it should be clearly understood to anyone skilled in the art that the form of the invention described above and shown in the figures is general in nature and not intended to limit the scope of the invention to any specific component measurement means within the scope and spirit of the appended claims.

I claim:

1. An apparatus for measuring the mass of hydrocarbon contained in a crude oil or natural gas production stream consisting primarily of crude oil, water, and gas, such apparatus comprising:

means forming a measurement section including a conduit for conducting a fluid mixture therethrough;

first measuring means mounted at said measurement section for measuring a temperature of the mixture and for generating a first signal representing said temperature;

second measuring means mounted at said measurement section for measuring the dielectric constant of the mixture and for generating a second signal representing said dielectric constant;

third measuring means mounted at said measurement section for measuring a density of the mixture and for generating a third signal representing said density;

means connected to said first, second, and third measuring means for receiving said first, second, and third signals, respectively, and, based upon said signals and upon a predetermined relation between hydrocarbon density and dielectric constant, for generating first output signal representing the volumetric water content of the mixture, a second output signal representing the volumetric hydrocarbon content in the mixture, a third output signal representing the hydrocarbon density in the mixture, and a fourth output representing the hydrocarbon mass in the mixture.

2. The apparatus of claim 1 further including:

a fourth measuring means mounted on the measurement section for measuring the flow rate of the mixture and for generating a fourth signal representing said flow rate;

wherein said receiving means includes means for generating, based upon said first, second, third, and fourth signals, a fifth output signal representing a mass flow rate of hydrocarbons.

3. An apparatus for measuring the water content in a liquid crude oil or natural gas production stream, such apparatus comprising:

means forming a measurement section including a conduit for conducting a fluid mixture therethrough;

first measuring means mounted at said measurement section for measuring a temperature of the mixture and for generating a first signal representing said temperature;

second measuring means mounted at said measurement section for measuring the dielectric constant of the mixture and for generating a second signal representing said dielectric constant;

third measuring means mounted at said measurement section for measuring a density of the mixture and for generating a third signal representing said density;

means connected to said first, second, and third measuring means for receiving said first, second, and third signals, respectively, and, based upon said signals and upon a predetermined relation between hydrocarbon density and dielectric constant, for generating first output signal representing the volumetric water content of the mixture and a second output signal representing the density of the hydrocarbon in the mixture.

4. An apparatus of claim 3 further including:

a fourth measuring means mounted on the measurement section for measuring the flow rate of the mixture and for generating a fourth signal representing said flow rate;

wherein said receiving means includes means for generating, based upon said first, second, third, and fourth signals, a third output signal representing a mass flow rate of the hydrocarbons.

* * * * *